United States Patent [19]

Rody et al.

[11] 4,127,586

[45] Nov. 28, 1978

[54] LIGHT PROTECTION AGENTS

[75] Inventors: Jean Rody, Basel; Hansjörg Heller, Riehen, both of Switzerland

[73] Assignee: Ciba-Geigy Corporation, Ardsley, N.Y.

[21] Appl. No.: 621,453

[22] Filed: Oct. 10, 1975

Related U.S. Application Data

[63] Continuation-in-part of Ser. No. 408,763, Oct. 23, 1973, abandoned, which is a continuation of Ser. No. 155,293, Jun. 21, 1971, abandoned.

[30] Foreign Application Priority Data

Jun. 19, 1970 [CH] Switzerland ............................ 9319/70

[51] Int. Cl.$^2$ .......................................... C07D 249/20
[52] U.S. Cl. ........................ 260/308 B; 260/45.8 NT
[58] Field of Search ..................................... 260/308 B

[56] References Cited

U.S. PATENT DOCUMENTS 3,823,112  7/1974  Ponder ............................ 260/308 B

FOREIGN PATENT DOCUMENTS 273,789 12/1963 Australia.
119,098  7/1966 Czechoslovakia .................. 260/308 B
878,362  9/1961 United Kingdom ................ 260/308 B
974,713 11/1964 United Kingdom ................ 260/308 B

OTHER PUBLICATIONS

Sowdey, Chem. Abstracts, vol. 62, col. 4822c (1965).
Geigy III, Chem. Abstracts, vol. 64, col. 14364–14365 (1966).
Geigy IV, Chem. Abstracts, vol. 63, col. 13506b (1965).

*Primary Examiner*—Paul M. Coughlan, Jr.
*Attorney, Agent, or Firm*—Vincent J. Cavalieri

[57] ABSTRACT

New 2-(2'-hydroxyphenyl)-benzotriazoles are used for protecting light-sensitive organic materials. They are prepared by diazotization of a 2-nitroaniline, coupling of the resulting diazo compound with a phenol and reduction of the resulting 2-nitroazo compound.

6 Claims, No Drawings

LIGHT PROTECTION AGENTS

The present invention relates to new 2-(2'-hydroxyphenyl)-benztriazole compounds, their use for protecting light-sensitive organic materials, especially high polymer materials, their use for the manufacture of UV-filters, and, as an industrial product, the organic material protected with the aid of these compounds against the harmful influence of light.

It has been found that new compounds of the formula I

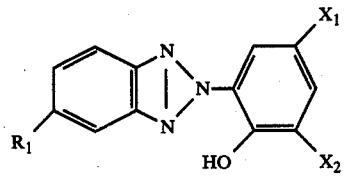

in which one of $X_1$ and $X_2$ denotes a secondary alkyl radical with 3–14 carbon atoms or the 1-phenylethyl group, the other of $X_1$ and $X_2$ denotes an alkyl group with 1–14 carbon atoms, the benzyl group, the 1-phenylethyl group, the cyclohexyl group, the cyclooctyl group or chlorine, and $X_2$ additionally also denotes hydrogen and $R_1$ denotes hydrogen, chlorine, methyl or methoxy, are particularly suitable for use as UV-absorbers in polymeric substrates.

The UV-absorbers of the o-hydroxyphenylbenztriazole class which have hitherto become known frequently only show a limited compatibility with the substrate in practical use. Furthermore they frequently show a certain volatility from the substrate at the high temperatures which are industrially customary for the incorporation process, and also at higher use temperatures, especially when one is dealing with substrates of low thickness, such as, for example, fibres, foils, films and stoving lacquers. It is also frequently not possible to incorporate higher UV-absorber concentrations homogeneously into the substrate, though this would be of advantage for the manufacture of UV-absorber-substrate concentrates (master batches) on the one hand, and for the manufacture of thin substrate layers of high filtering action, on the other. The latter case is of particular industrial importance in the coating of paper and foil material against damage by UV-radiation.

Surprisingly, the new UV-absorbers according to the invention now show significantly improved substrate compatibility as compared to the previously known compounds. This has made it possible to incorporate the new UV-absorbers into the substrate in high concentrations and nevertheless to achieve homogeneous distribution, whereby the abovementioned technical problems can be solved satisfactorily. Equally, the compounds according to the invention, especially those in which one of $X_1$ and $X_2$ denotes the phenylethyl or cyclooctyl group, show a considerably lesser volatility from the substrate on warming the latter to higher temperatures. They are therefore particularly suitable for use in plastics which are exposed to higher processing temperatures or use temperatures.

It has also been found, unexpectedly, that the new UV-absorbers in higher concentrations show a better light protection action than the previously known UV-absorbers at the same concentrations.

In the formula I, one of $X_1$ or $X_2$ for example denotes a secondary alkyl radical with 3 to 14 carbon atoms, such as the iso-propyl, sec-butyl, sec.-amyl, sec.-hexyl, sec.-octyl, seco.-nonyl, sec.-decyl or sec.-tetradecyl radical.

The other of $X_1$ and $X_2$ in formula I for example denotes an alkyl radical with 1 to 14 carbon atoms, such as the methyl, ethyl, propyl, iso-propyl, n-butyl, sec.-butyl, tert-butyl, n-pentyl, sec.-pentyl, tert-pentyl, hexyl, tert-hexyl, heptyl, octyl, iso-octyl, tert-octyl, nonyl, sec.-nonyl, tert-nonyl, sec.-dodecyl, tert-dodecyl or the sec.-tetradecyl radical.

Preferred compounds of the formula I are those in which one of $X_1$ and $X_2$ denotes a secondary alkyl radical with 3 to 14 carbon atoms or the 1-phenylethyl group, and the other of $X_1$ and $X_2$ denotes an alkyl group with 1 to 14 carbon atoms, 1-phenylethyl, cyclohexyl or cyclooctyl, and $R_1$ denotes hydrogen or chlorine.

Particularly preferred compounds of the formula I are those in which one of $X_1$ and $X_2$ denotes an iso-propyl or secondary-butyl group, the other of $X_1$ and $X_2$ denotes sec.-butyl, tert-butyl, tert-amyl, tert-octyl, sec.-nonyl or tert-nonyl group, the 1-phenylethyl group, the cyclohexyl or the cyclooctyl group, and $R_1$ denotes hydrogen or chlorine.

The compounds of the formula I in which one of $X_1$ and $X_2$ denotes sec-butyl or 1-phenylethyl, the other of $X_1$ and $X_2$ denotes methyl, iso-propyl, sec-butyl, tert-butyl tert-amyl, cyclohexyl, 1-phenylethyl or chlorine and $X_2$ additionally denotes hydrogen and $R_1$ denotes hydrogen, chlorine, methyl or methoxy, are particularly suitable for stabilising polyolefines.

The compounds of the formula I in which one of $X_1$ and $X_2$ denotes a secondary alkyl radical with 4 to 9 carbon atoms or the 1-phenylethyl group and the other of $X_1$ and $X_2$ denotes an alkyl group with 1 to 9 carbon atoms, the cyclohexyl group, the cyclooctyl group or the 1-phenylethyl group, and $R_1$ denotes hydrogen or chlorine, and $X_1$ and $X_2$ together contain at least 8 carbon atoms, are particularly suitable for stabilising lacquers and protective coatings.

Another embodiment of the invention are compounds of the formula I

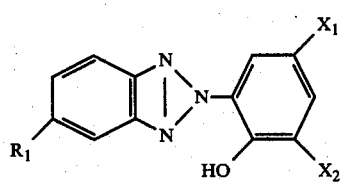

in which one of $X_1$ and $X_2$ denotes a secondary alkyl radical with 3 to 14 carbon atoms or the 1-phenylethyl group, and the other of $X_1$ and $X_2$ denotes an alkyl group with 1 to 14 carbon atoms, the benzyl group, the 1-phenylethyl group, the cyclohexyl group, the cyclooctyl group or chlorine, and $X_2$ additionally also denotes hydrogen and $R_1$ denotes hydrogen, chlorine, methyl or methoxy, provided that, if $X_1$ is 1-phenylethyl, $X_2$ is not hydrogen.

The compounds of the formula I in which one of $X_1$ and $X_2$ denotes sec.-butyl or sec.-amyl, the other of $X_1$ and $X_2$ denotes sec.-butyl, tert.-butyl, sec.-amyl, tert.-amyl, cyclohexyl or cyclooctyl, $X_2$ additionally also denotes hydrogen and $R_1$ denotes hydrogen, chlorine or methoxy, are particularly suitable for coating foil material.

The new compounds of the formula I are obtained in a manner which is in itself known by diazotisation of 2-nitroaniline or appropriately substituted 2-nitroanilines, coupling of the resulting diazo compound with an appropriately substituted phenol, and reduction of the resulting 2-nitroazo compound by means of zinc powder in alkaline solution to give the desired benztriazole. The substituted phenols coupling in the ortho-position, which are required as intermediate products, are in part commercially available or can be manufactured according to known methods, for example by acid-catalysed alkylation of phenol or of a o-substituted or p-substituted phenol with an optionally aryl-substituted olefine. If longer-chain olefines are employed in this alkylation, mixtures of various alkylation products, in which the sec.-alkyl chain is linked to the phenol radical via various carbon atoms, are obtained in the case of the acid-catalysed reaction, because of the isomerisation of the olefine which occurs. Such a phenol-isomer mixture can be employed directly for the manufacture of the compounds according to the invention, of the formula I. An end product is thereby obtained which represents a mixture of various compounds of the formula I, which differ from one another in the branching of the secondary alkyl group in the phenol radical. The use of such a mixture as a UV-absorber can in certain cases even be of advantage, since such mixtures display particularly good substrate compatibility.

Possible carrier materials for the new compounds of the formula I are above all organic polymers, including both thermoplastic polymers and curable synthetic resins (thermosetting polymers). Both wholly synthetic polymers and natural polymers, as well as their polymer-homologous chemical modification products can be used. Amongst the wholly synthetic polymers, pure addition polymers and pure condensation polymers, but also condensation polymers crosslinked by addition polymerisation, can be employed.

The addition polymers which can be used as carrier materials for the new light protection agents can be classified under the following main types:

1. Homopolymers and copolymers of vinyl vinylidene monomers which are converted by radical, ionic or metalorganic polymerisation initiators into the corresponding polymers. Examples of such polymers, the polymers of which are suitable for use as carrier materials, are:

Polymerisable ethylenically unsaturated halogenated hydrocarbon compounds, such as, for example, vinyl chloride, vinyl fluoride and vinylidene chlorides, polymerisable hydrocarbons with a double bond capable of addition, such as, for example, styrene, isobutylene, ethylene, propylene, 1-butene, 3-methyl-1-butene and 4-methyl-1-pentene, where both the atactic and also the tactic polymers can be used, $\alpha,\beta$-unsaturated polymerisable carboxylic acids and their functional derivatives, such as acrylic acid, methacrylic acid, acrylonitrile, alkyl esters and amides of acrylic acid and methacrylic acid, for example the methyl, ethyl and butyl esters of methacrylic acid and of acrylic acid.

Further carrier materials which can also be used advantageously for the new light protection agents are copolymers of the abovementioned acrylic acid derivatives, such as are, for example, used for the manufacture of thermoplastic acrylic resin lacquers. They are also used advantageously in heat-curable acrylic resin lacquers, which are composed of a copolymer of acrylic acid and one or more of its derivatives, and a melamine-formaldehyde resin.

Polymerisable acyl derivatives of ethylenically unsaturated alcohols and amines can also be used, wherein acyl radicals of alkanecarboxylic acids and alkenecarboxylic acids with up to 18 carbon atoms and of aromatic monocyclic carboxylic acids, such as benzoic acids and of phthalic acids, as well as of cyclic carbonic acid imides, such as, for example, those of cyanuric acid, are employed. Examples are allyl phthalate, polyallyl-melamines, vinyl acetate, vinyl stearate, vinyl benzoate and vinyl maleate, polymerisable polyenes with conjugated double bonds, such as butadiene, isoprene, chloroprene, sorbic acid and its esters.

2. Homopolymers and copolymers of epoxides are produced by acid-catalysed or base-catalysed curing. For example, the polymers of bis-glycidyl-ethers of the geminal bis-(p-hydroxyphenyl)-alkanes and -cycloalkanes can be used in this category.

3. Homopolymers and copolymers of lactams and lactones, such as, for example, the polymers of ε-caprolactam or lauryl-lactam.

4. Homopolymers and copolymers of aldehydes, such as, for example, of formaldehyde and acetaldehyde, such as polyoxymethylene and polyoxyethylene.

5. Reaction products of isocyanates with hydroxy compounds and/or amino compounds, such as, for example, those of diisocyanates or polyisocyanates with difunctional or polyfunctional hydroxyl or amino compounds. This class also includes the polyurethanes and polyureas which are produced by reaction of diisocyanates with polyesters and/or polyethers containing hydroxyl groups.

The condensation polymers which can be used as carrier materials for the new compounds of the formula I, are, amongst others, polyesters and polyamides. Linear thermoplastic polycondensates and copolycondensates, which are derived from dicarboxylic acid and organic dihydroxy derivatives or organic diamines on the one hand, and hydroxycarboxylic acids or aminocarboxylic acids on the other, should here be mentioned. Linear polycondensates are, for example, the fibre-forming polymers of $\omega,\omega'$-dicarboxylic acids and $\omega,\omega'$-dihydroxy compounds, or $\omega,\omega'$-diamines, as well as of $\omega$-hydroxycarboxylic acids or of $\omega$-aminocarboxylic acids which are derived from saturated, aliphatic, cycloaliphatic and carbocyclic non-fused aromatic carboxylic acids.

The following components are, for example, suitable for the manufacture of linear condensation products: adipic acid-hexamethylenediamine, sebacic acid-hexamethylenediamine, adipic acid/sebacic acid-hexamethylenediamine, terephthalic acid-ethylene glycol, terephthalic acid-1,4-dimethylolcyclohexane, and 10-aminodecanecarboxylic acid.

Crosslinked polycondensates used as carrier materials are heat-curable and are especially produced by condensation of aldehydes with polyfunctional compounds capable of condensation. Formaldehyde condensates with phenols, ureas and melamines may be mentioned.

Further carrier materials are alkyd resins which are obtained by reaction of phthalic anhydride with mixtures of diols and triols, as well as their mixtures with melamine-formaldehyde condensates.

Amongst the condensation polymers which are crosslinked by subsequent addition polymerisation, the polyester resins should be mentioned. These are polycondensates of at least one unsaturated organic dicarboxylic acid with polyhydric alcohols, which can be modified by saturated and/or dicarboxylic acid and their anhydrides, and which can be crosslinked by adding compounds having double bonds capable of addition. In these it is, for example, possible to use maleic acid or its anhydride, itaconic acid, citraconic acid or fumaric acid as unsaturated dicarboxylic acids, succinic acid, adipic acid, azelaic acid or sebacic acid as saturated dicarboxylic acids, isophthalic acid or the anhydrides of phthalic acid, tetrachlorophthalic acid or tetrabromophthalic acid and 1,2,3,4,7,7-hexachloro-dicyclo-(2,2,1)-hept-2-ene-5,6-dicarboxylic acid anhydride as aromatic dicarboxylic acids, ethylene glycol, propylene glycol, diethylene glycol, neopentyl glycol or trimethylpentanediol as alcohols, and styrene, p-chlorostyrene, diallyl phthalate, methyl methacrylate, vinyltoluene or diallyl cyanurate as crosslinking agents.

The naturally occurring polymers which can be used as carrier materials for the new light protection agents are, for example, polysaccharides, such as cellulose, or rubber and proteins.

Amongst the polymer-homologous chemically modified synthetic polymers, the reaction products of polyvinyl alcohols with aldehydes, such as polyvinyl butyral, and the saponification products of polyvinyl esters should, for example, be mentioned. Polymer-homologous chemically modified natural polymers as carrier materials for the new light protection agents are, for example, the cellulose esters and cellulose ethers, such as the cellulose esters of acetic acid, propionic acid and benzoic acid having an average of 1 to 3 acyl groups per glucose unit.

The polymers mentioned in the above list are also used as mixtures as carriers of the new light protection agents in material compositions according to the invention.

Particularly valuable material compositions according to the invention contain, as carriers of the new light protection agents, light-sensitive polymers which are derived from styrene, vinyl chloride, vinyl fluoride, acrylonitrile, olefines, acrylic acid esters and/or methacrylic acid esters, as well as polyesters or polyamides, polyester resins, polyacetals, polycarbonates, polyurethanes, cellulose ethers and cellulose esters, as well as mixtures of melamine-formaldehyde condensates with alkyd resins. Particularly preferred carriers are polymeric hydrocarbons, such as, for example, high pressure polyethylene and low pressure polyethylene, polypropylene, polybutene, poly(-3-methyl-1-butene), poly(4-methyl-1-pentene), ethylene-butene copolymers, ethylene-propylene copolymers, ethylene-propylene terpolymers and propylene-ethylene polyallomers.

Apart from these polymers, further possible carriers are natural and synthetic light-sensitive waxes, fats and oils, and also complex systems, such as coated foil material, emulsions which contain light-sensitive fatty substances, and emulsions or dispersions of the abovementioned polymers.

Suitable compounds for use in unsaturated polyester resins, polyester resins containing chlorine, acetylcellulose, PVC, polystyrene, acrylic resins, vinyl copolymers and vinylacrylic copolymers are above all compounds of relatively low molecular weight but high specific absorption coefficient, such as, for example: 2-(2-hydroxy-5-isopropylphenyl)-benztriazole, 2-(2-hydroxy-3,5-di-isopropylphenyl)-benztriazole, 2-(2-hydroxy-5-sec.butylphenyl)-benztriazole, 2-(2-hydroxy-3-chloro-5-sec.butylphenyl)-benztriazole, 2-(2-hydroxy-3-sec.butyl-5-chlorophenyl)-benztriazole and 2-(2-hydroxy-5-sec.amylphenyl)-benztriazole.

Suitable compounds for stabilising polyolefines, such as polypropylene and polyethylene, are above all compounds of good substrate compatibility and low volatility, such as, for example: 2-[2-hydroxy-3-(1-phenylethyl)-5-methylphenyl]-benztriazole, 2-[2-hydroxy-3-(1-phenylethyl)-5-methylphenyl]-5-chloro-benztriazole, 2-(2-hydroxy-3-tert.butyl-5-isopropylphenyl)-5-chloro-benztriazole, 2-(2-hydroxy-3-tert.amyl-5-isopropylphenyl)-benztriazole, 2-(2-hydroxy-3-tert.butyl-5-sec.-butylphenyl)-benztriazole, 2-(2-hydroxy-3-tert.butyl-5-sec.butylphenyl)-5-chloro-benztriazole, 2-(2-hydroxy-3-tert.amyl-5-sec.butylphenyl)-benztriazole, 2-(2-hydroxy-3-tert.amyl-5-sec.butylphenyl)-5-chloro-benztriazole, 2-[2-hydroxy-5-(1-phenylethyl)-phenyl]-benztriazole, 2-[2-hydroxy-5-(1-phenylethyl)-phenyl]-5-chloro-benztriazole, 2-[2-hydroxy-3-(1-phenylethyl)-5-chlorophenyl]-benztriazole, 2-[2-hydroxy-3-(1-phenylethyl)-5-chlorophenyl]-5-chlorobenztriazole, 2-(2-hydroxy-3-tert.butyl-5-sec.butylphenyl)-5-methyl-benztriazole and 2-(2-hydroxy-3-tert.butyl-5-sec.butylphenyl)-5-methoxy-benztriazole.

For lacquer systems, such as TPA lacquers or stoving lacquers, compounds of very good solubility and minimum volatility are above all suitable, such as, for example: 2-(2-hydroxy-3-cyclohexyl-5-sec.butylphenyl)-benztriazole, 2-(2-hydroxy-3-cyclohexyl)-5-sec.butylphenyl)-5-chloro-benztriazole, 2-(2-hydroxy-3-cyclooctyl-5-sec.butylphenyl)-benztriazole, 2-(2-hydroxy-3-cyclooctyl-5-sec.butylphenyl)-5-chloro-benztriazole, 2-[2-hydroxy-3-(1-phenylethyl)-5-sec.butylphenyl]-benztriazole, 2-[2-hydroxy-3-(1-phenylethyl-5-sec.-butylphenyl]-5-chloro-benztriazole and 2-(2-hydroxy-3,5-di-sec.nonylphenyl)-benztriazole.

Particularly suitable compounds for coating foil material are compounds of extremely good solubility and a low tendency to crystallisation, such as, for example: 2-(2-hydroxy-3-tert.butyl-5-sec.butylphenyl)-benztriazole, 2-(2-hydroxy-3-tert.amyl-5-sec.butylphenyl)-benztriazole, 2-(2-hydroxy-3-tert.butyl-5-sec.butylphenyl)-5-chloro-benztriazole, 2-(2-hydroxy-3-tert.amyl-5-sec.butylphenyl)-5-chloro-benztriazole, 2-(2-hydroxy-3,5-di-sec.butylphenyl)-benztriazole, 2-(2-hydroxy-3,5-di-sec.butylphenyl)-5-chloro-benztriazole and 2-(2-hydroxy-3-cyclooctyl-5-sec.butylphenyl)-benztriazole.

The molecular weight of the abovementioned polymers plays a subordinate role, as long as it lies within the limiting values required for the characteristic mechanical properties of the polymers in question. It can be 1000 to several millions, depending on the polymer. The incorporation of the new compounds into these polymers is, for example, effected, depending on the nature of the polymer, by incorporating at least one of these compounds and, if appropriate, further additives, into the melt in accordance with the methods customary in the art, before or during shaping, or by dissolving in the corresponding monomers before polymerisation, or by dissolving the polymer and the additives in solvents and subsequently evaporating the latter. The new compounds can also be absorbed from baths, for example from aqueous dispersions, onto thinner carrier structures, such as films or filaments.

The light protection agents according to the invention are particularly advantageously incorporated into weakly basic, neutral or acid carriers.

The light-sensitive materials can also be protected against the harmful effect of light by coating them with a protective layer, for example with a lacquer, containing at least one benztriazole according to the invention, or covering them with structures containing such light protection agents, such as films, panes or sheets. In both these cases, the amount of the added light protection agent is advantageously 10–30% (relative to the protective layer material) in the case of protective layers of less than 0.01 mm thickness, and 1–10% in the case of protective layers of 0.01–0.1 mm thickness.

As further additives together with which the stabilisers usable according to the invention may be employed, there may be mentioned:

1. Antioxidants of the aminoaryl and hydroxyaryl series. Amongst the latter, the sterically hindered phenol compounds should be mentioned, for example: 2,2'-thiobis-(4-methyl-6-tert.butylphenol), 4,4'-thiobis-(3-methyl-6-tert.butylphenol), 2,2'-methylene-bis-(4-methyl-6-tert.butylphenol), 2,2'-methylene-bis-(4-ethyl-6-tert.butylphenol), 4,4'-methylene-bis-(2-methyl-6-tert.butylphenol), 4,4'-butylidene-bis-(3-methyl-6-tert.butylphenol), 2,2'-methylene-bis-[4-methyl-6-(α-methylcyclohexyl)-phenol], 2,6-di-(2-hydroxy-3-tert.butyl-5-methylbenzyl)-4-methyl-phenol, 2,6-di-tert.butyl-4-methylphenol, 1,1,3-tris-2-methyl-(4-hydroxy-5-tert.butyl-phenyl)-butane, 1,3,5-trimethyl-2,4,6-tri-(3,5-di-tert.butyl-4-hydroxy-benzyl)-benzene, esters of β,β'-bis-(3-tert.butyl-4-hydroxy-phenyl)-butyric acid with monohydric or polyhydric alcohols, such as octadecanol or hexanediol, esters of β-4-hydroxy-3,5-di-tert.butylphenyl-propionic acid with monohydric or polyhydric alcohols, such as methanol, ethanol, octadecanol, hexanediol, nonanediol, trimethylhexanediol, thiodiethylene glycol, trimethylolethane or pentaerythritol, 2,4-bis-octylmercapto-6-(4-hydroxy-3,5-di-tert.butylanilino)-s-triazine, 2,4-bis-(4-hydroxy-3,5-di-tert.butylphenoxy)-6-octylmercapto-s-triazine, 1,1-bis-(4-hydroxy-2-methyl-5-tert.butyl-phenyl)-3-dodecyl-mercaptobutane, 4-hydroxy-3,5-di-tert.butylbenzyl-phosphonic acid ester, such as the dimethyl, diethyl or dioctadecyl ester, (3-methyl-4-hydroxy-5-tert.butylbenzyl)-malonic acid dioctadecyl ester, S-(3,5-dimethyl-4-hydroxybenzyl)-thioglycollic acid octadecyl ester, esters of bis-(3,5-di-tert.butyl-4-hydroxybenzyl)-malonic acid, such as the didodecyl ester, the dioctadecyl ester, the 2-dodecylmercaptoethyl ester and the p-tert.octylphenyl ester.

Amongst the aminoaryl derivatives, aniline and naphthylamine derivatives should be mentioned, as well as their heterocyclic derivatives, for example phenyl-1-naphthylamine, phenyl-2-naphthylamine, N,N'-diphenyl-p-phenylenediamine, N,N'-di-2-naphthyl-p-phenylenediamine, N,N'-di-sec.butyl-p-phenylenediamine, 6-ethoxy-2,2,4-trimethyl-1,2-dihydroquinoline, 6-dodecyl-2,2,4-trimethyl-1,2-dihydroquinoline, monooctyliminodibenzyl and dioctyliminodibenzyl, and polymerised 2,2,4-trimethyl-1,2-dihydroquinoline, though on combined use of the compounds of the formula I with the abovementioned aminoaryl derivatives the stabilised polymer appears discoloured.

2. Other UV-absorbers and light protection agents, such as:
   (a) 2,4-Bis-(2'-hydroxyphenyl)-6-alkyl-s-triazines, for example the 6-ethyl, 6-undecyl or 6-heptadecyl derivative.
   (b) 2-Hydroxy-benzophenones, for example the 4-hydroxy, 4-methoxy, 4-octoxy, 4-decyloxy, 4-dodecyloxy, 2'-hydroxy-4-methoxy, 4,2',4'-trihydroxy or 2'-hydroxy-4,4'-dimethoxy derivative.
   (c) 1,3-Bis-(2'-hydroxy-benzoyl)-benzenes, for example 1,3-bis-(2'-hydroxy-4'-ethoxy-benzoyl)-benzene, 1,3-bis-(2'-hydroxy-4'-hexyloxy-benzoyl)-benzene, 1,3-bis-(2'-hydroxy-4'-octoxy-benzoyl)-benzene, 1,3-bis-(2'-hydroxy-4'-dodecyloxybenzoyl)-benzene and 1,3-bis-(2',4'-dihydroxy-benzoyl)-benzene.
   (d) Aryl esters of optionally substituted benzoic acids, such as, for example, phenyl salicylate, octylphenyl salicylate, benzoyl-resorcinol, dibenzoyl-resorcinol, 3,5-di-tert.butyl-4-hydroxybenzoic acid (2,4-tert.butylphenyl) ester or octadecyl ester.
   (e) Acrylates, for example α-cyano-β,β-diphenylacrylic acid ethyl ester or isooctyl ester, 4-methoxy-α-carbomethoxycinnamic acid methyl ester, α-cyano-β-methyl-p-methoxycinnamic acid methyl ester or butyl ester, and N-(β-carbomethoxyvinyl)-2-methylindoline.
   (f) Nickel compounds, for example nickel complexes of 2,2'-thiobis-(4-tert.octylphenol), such as the 1:1 and 1:2 complex, optionally with other ligands, such as n-butylamine, nickel complexes of bis-(4-tert.octylphenyl)-sulphone, such as the 2:1 complex, optionally with other ligands, such as 2-ethylcaproic acid, nickel dibutyldithiocarbamate, nickel salts of 4-hydroxy-3,5-di-tert.butylbenzyl-phosphonic acid monoalkyl esters, such as the methyl, ethyl or butyl esters, and the nickel complex of 2-hydroxy-4-methyl-phenyl-undecyl ketoneoxime.
   (g) Oxalic acid diamides, for example 4,4'-di-octyloxyoxalanilide, 2,2'-di-octyloxy-5,5'-di-tert.butyl-oxalanilide and 2,2'-di-dodecyloxy-5,5-di-tert.butyl-oxalanilide.

3. Phosphites, such as triphenylphosphite, diphenylalkylphosphite, phenyldialkylphosphites, trinonylphenylphosphite, trilaurylphosphite, trioctadecylphosphite, 3,9-di-isodecyloxy-2,4,8,10-tetraoxa-3,9-diphosphaspiro-(5,5)-undecane and tris-(4-hydroxy-3,5-di-tert.butylphenyl)-phosphite.

4. Nucleating agents, such as 4-tert.butylbenzoic acid, adipic acid, and diphenylacetic acid. 5. Compounds which destroy peroxide, such as esters of β-thiodipropionic acid, for example the lauryl, stearyl, mirystyl or tridecyl ester. Salts of 2-mercaptobenzimidazole, for example the zinc salt, and diphenylthiourea. 6. Other additives, such as plasticisers, antistatic agents, flameproofing agents, inorganic and organic pigments, carbon black, asbestos, glass fibres, kaolin and talc.

When using the stabilisers according to the invention in combination with phenolic antioxidants, particularly good stabilising effects are achieved if compounds which destroy peroxides, such as higher alkyl esters of thiopropionic acid, are employed simultaneously, since these compounds which destroy peroxides not only, as is known, show synergism with the phenolic antioxidants, but also show synergism with the stabilisers of the formula I.

The invention is described in more detail in the examples which follow.

EXAMPLE 1

138 g of o-nitroaniline are suspended in 500 ml of water and 250 ml of concentrated hydrochloric acid and diazotised at 0° – 5° C with a solution of 69 g of sodium nitrite in 200 ml of water.

A solution of 206 g of 2-tert.butyl-4-sec.butylphenol in 200 ml of light benzine (boiling point 80° - 95° C) is added to the resulting diazonium salt solution, with thorough stirring, and thereafter a solution of 200 g of crystalline sodium acetate in 300 ml of water is allowed to run in over the course of approx. 1 hour. The reaction mixture is thoroughly stirred for 5 hours at 20° C and the organic phase is then separated from the aqueous phase, which is discarded.

300 ml of isopropanol, 300 ml of water and 200 ml of concentrated sodium hydroxide solution are added to the organic phase, the mixture is warmed to 40° C and 150 g of zinc dust are introduced in portions over the course of approx. 1 hour, with good stirring. Thereafter the reaction mixture is warmed to 70° C for 3 hours and cooled to 20° C, and rendered acid to Congo Red with excess hydrochloric acid. The organic phase is separated from the aqueous phase and the solvent is distilled off in vacuo. The residue is recrystallised from isopropanol, with the addition of decolourising charcoal. 2-(2-Hydroxy-3-tert.butyl-5-sec.butylphenyl)-benztriazole of melting point 84° C is thus obtained.

The 2-hydroxyphenylbenztriazoles indicated in Table I below are obtained if, following the same procedure, the equivalent quantities of the corresponding o-nitroaniline and phenol are employed as starting products. In this Table, the analytically pure substances are characterised by the melting point (uncorrected). Liquid compounds, or crude products which have, by reprecipitation and purification with animal charcoal, been brought to a degree of purity which suffices for the application but is inadequate as regards the melting point, are characterised by their spectral properties, quoting the wavelength of the longest-wavelength maximum ($\lambda$) and the molar extinction coefficient ($\epsilon$) of a chloroform solution (1 mg of substance in 100 ml of chloroform, layer thickness 1 cm).

Table I

General formula

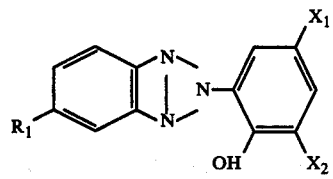

| No. | $X_1$ | $X_2$ | R | Melting point | Spectral properties |
|---|---|---|---|---|---|
| 1 | $CH_3$ | —CH—Ph<br>\|<br>$CH_3$ | H | 120° C | — |
| 2 | $CH_3$ | —CH—Ph<br>\|<br>$CH_3$ | Cl | 120° C | — |
| 3 | iso-propyl | H | H | 84° C | — |
| 4 | iso-propyl | iso-propyl | H | 87° C | — |
| 5 | iso-propyl | iso-propyl | Cl | 65° C | — |
| 6 | iso-propyl | tert. butyl | H | 113° C | — |
| 7 | iso-propyl | tert. butyl | Cl | 105° C | — |
| 8 | iso-propyl | tert. amyl | H | 54° C | — |
| 9 | sec. butyl | H | H | 70° C | — |
| 10 | sec. butyl | Cl | H | 103° C | — |
| 11 | sec. butyl | tert. butyl | H | 84° C | — |
| 12 | sec. butyl | tert. butyl | Cl | 70° C | — |
| 13 | sec. butyl | tert. amyl | H | 57–58° C | — |
| 14 | sec. butyl | tert. amyl | Cl | 74° C | — |
| 15 | sec. butyl | cyclohexyl | H | 84° C | — |
| 16 | sec. butyl | cyclohexyl | Cl | 75° C | — |
| 17 | sec. butyl | cyclooctyl | H | liquid | $\lambda_{max}$346 nm; $\epsilon_{molar}$=1520 |
| 18 | sec. butyl | cyclooctyl | Cl | 62° C | — |
| 19 | sec. butyl | —CH—Ph<br>\|<br>$CH_3$ | Cl | 90° C | — |
| 20 | sec. butyl | —CH—Ph<br>\|<br>$CH_3$ | H | 51° C | — |
| 21 | sec. butyl | sec. butyl | H | 36–38° C | — |
| 22 | sec. butyl | sec. butyl | Cl | liquid | $\lambda_{max}$353 nm; $\epsilon_{molar}$=1570 |
| 23 | Cl | sec. butyl | H | 73° C | — |
| 24 | —CH$\langle^{C_2H_5}_{C_2H_5}$ | H | H | 90° C | — |
| 25 | —CH—Ph<br>\|<br>$CH_3$ | H | H | 114° C | — |
| 26 | —CH—Ph<br>\|<br>$CH_3$ | H | Cl | 110° C | — |
| 27 | Cl | —CH—Ph<br>\|<br>$CH_3$ | H | 101° C | — |
| 28 | Cl | —CH—Ph<br>\|<br>$CH_3$ | Cl | 105° C | — |

Table I-continued

General formula

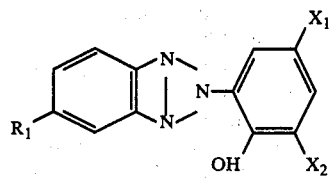

| No. | $X_1$ | $X_2$ | R | Melting point | Spectral properties |
|---|---|---|---|---|---|
| 29 | sec. nonyl | sec. nonyl | H | liquid | $\lambda_{max}$346 nm; $\epsilon_{molar}$=1610 |
| 30 | sec. butyl | tert. butyl | $CH_3$ | — | $\lambda_{max}$344 nm; $\epsilon_{molar}$=1670 |
| 31 | sec. butyl | tert. butyl | $OCH_3$ | — | $\lambda_{max}$348 nm; $\epsilon_{molar}$=1960 |
| 32 | sec. decyl | H | H | — | $\lambda_{max}$344 nm; $\epsilon_{molar}$=1560 |
| 33 | $CH_3$ | sec. tetradecyl | H | — | $\lambda_{max}$346 nm; $\epsilon_{molar}$=1650 |
| 34 | $CH_3$ | sec. dodecyl | Cl | — | $\lambda_{max}$352 nm; $\epsilon_{molar}$=1690 |
| 35 | sec. butyl | sec. octyl | $OCH_3$ | liquid | $\lambda_{max}$347 nm; $\epsilon_{molar}$=2060 |
| 36 | tert. butyl | sec. butyl | H | 80° C | |
| 37 | tert. butyl | sec. butyl | Cl | 44–45° C | |
| 38 | tert. butyl | sec. butyl | $OCH_3$ | 70° C | |
| 39 | tert. butyl | sec. butyl | $CH_3$ | 78° C | |
| 40 | —CH—Ph<br>   |<br>  $CH_3$ | sec. butyl | H | | $\lambda_{max}$345 nm; $\epsilon_{molar}$=16300 |
| 41 | tert. amyl | sec. butyl | H | 70° C | |
| 42 | tert. amyl | sec. butyl | Cl | 71° C | |
| 43 | sec. tetradecyl | sec. butyl | H | | $\lambda_{max}$344 nm; $\epsilon_{molar}$=16200 |

EXAMPLE 2

100 parts of polyethylene of density 0.917 are homogeneously mixed, at 180° C, with 0.5 part of a UV-absorber of the table which follows and 0.2 part of 3-(3',5'-di-t-butyl-4'-hydroxyphenyl)-propionic acid octadecyl ester, in a Brabender plastograph. The mass thus obtained is pressed in a platen press at 260° C to give 1 mm thick sheets. Test specimens of size 10 × 10 cm are punched from these sheets. The volatility of the individual UV-absorbers are determined on these test specimens in the following manner: the test specimens are warmed to 100° C in a circulating air oven and at certain intervals of time are examined for their residual content of UV-absorber. For this purpose, the test specimens are extracted with chloroform and the content of UV-absorber in the chloroform solution is measured spectroscopically. As can be seen from Table II below, the new compounds are much less volatile than the previously known Compound 1. This compound was selected as the comparison product, because it gives the best result in this test from amongst the various known commercially available products of the o-hydroxyphenylbenztriazole category.

Table II

| No | UV-Absorber | 24 hrs | 48 hrs | 72 hrs | 96 hrs | 120 hrs |
|---|---|---|---|---|---|---|
| | | Residual content of UV-Absorber in % after hrs. in circulating air oven at 100° C | | | | |
| 1 | 2-(2-Hydroxy-3,5-di-tert. amylphenyl)-benztriazole (comparison compound) | 73 | 68 | 57 | 49 | 41 |
| 2 | 2-[2-Hydroxy-3-(1-phenylethyl)-5-methylphenyl]-benztriazole | 100 | 87 | 83 | 76 | 63 |
| 3 | 2-[2-Hydroxy-3-(1-phenylethyl)-5-methylphenyl]-5-chlorobenztriazole | 100 | 97 | 97 | 97 | 97 |
| 4 | 2-[2-Hydroxy-3-cyclohexyl-5-sec-butylphenyl]-benztriazole | 95 | 91 | 89 | 80 | 78 |
| 5 | 2-(2-Hydroxy-3-cyclohexyl-5-sec-butyphenyl)-5-chlorobenztriazole | 100 | 100 | 100 | 100 | 100 |

EXAMPLE 3

100 parts of polypropylene of density 0.90 are homogeneously mixed at 200° C with 0.5 part of a UV-absorber of the table which follows, 0.2 part of bis-(5-t-butyl-4-hydroxy-2-methylphenyl)-sulphide, 0.2 part of dilauryl-thiodipropionate and 0.2 part of trioctadecyl-phosphite, in a Brabender plastograph. The mass thus obtained is pressed in a platen press at 260° C to give 1 mm thick sheets, from which test specimens of size 10 × 10 cm are punched. The volatility of the UV-absorbers incorporated in these test specimens is tested as described in Example 2.

The Table III which follows shows that the volatilities of the new compounds is much less than that of the commercially available product which gives the best result in this test (Compound 1).

Table III

| No | UV-Absorber | 24 hrs | 48 hrs | 72 hrs | 96 hrs | 120 hrs |
|---|---|---|---|---|---|---|
| | | Residual content of UV-Absorber in % after hrs. in circulating air oven at 100° C | | | | |
| 1 | 2-(2-Hydroxy-3,5-di-t-butylphenyl)-benztriazole (comparison compound) | 86 | 72 | 64 | 56 | 46 |
| 2 | 2-[2-Hydroxy-3-(1-phenylethyl)-5-methylphenyl]-benztriazole | 94 | 89 | 75 | 71 | 71 |

Table III-continued

| | | Residual content of UV-Absorber in % after hrs. in circulating air oven at 100° C | | | | |
|---|---|---|---|---|---|---|
| No | UV-Absorber | 24 hrs | 48 hrs | 72 hrs | 96 hrs | 120 hrs |
| 3 | 2-[2-Hydroxy-3-(1-phenylethyl)-5-methylphenyl]-5-chlorobenztriazole | 100 | 100 | 97 | 95 | 92 |
| 4 | 2-(2-Hydroxy-3-cyclohexyl-5-sec-butylphenyl)-benztriazole | 100 | 95 | 84 | 82 | 80 |
| 5 | 2-(2-Hydroxy-3-cyclohexyl-5-sec butylphenyl)-5-chlorobenztriazole | 100 | 100 | 100 | 100 | 100 |

EXAMPLE 4

0.5 part (= 2% calculated relative to the solids content of the lacquer) of a UV-absorber from Table IV below is added to 100 parts of a thermoplastic acrylic resin lacquer of the following composition: 14.4 parts of Plexigum M 347 (polyacrylic resin of Messrs. Röhm and Haas), 18.4 parts of methyl ethyl ketone, 38.6 parts of toluene, 18.5 parts of ethylglycol acetate, 3.3 parts of EAB 381-2 (acetobutyrate of Messrs. Eastman Kodak), and 6.8 parts of butyl benzyl phthalate. The resulting lacquer formulation is applied by means of a centrifugal lacquer coater onto an optically clean sheet of glass of size 40 × 40 mm to give a 10 μ thick layer. The lacquer film thus obtained is measured spectrophotometrically in comparison to a film manufactured in exactly the same way but not containing any UV-absorber.

The lacquer layer on the sheet of glass is now stoved in a circulating air oven for 30 minutes at 140° C. Thereafter the residual content of UV-absorber in the lacquer layer is determined spectrophotometrically. As can be seen from Table IV below, the new compounds prove much less volatile on stoving the lacquer than does the best commercially available product (Compound 1).

Table IV

| No. | UV-Absorber | Residual content after 30 minutes stoving at 140° C, in % |
|---|---|---|
| 1 | 2-(2-Hydroxy-3,5-di-tert.-amylphenyl)-benztriazole (comparison compound) | 25 |
| 2 | 2-[2-Hydroxy-3-(1-phenylethyl)-5-methylphenyl]-5-chlorobenztriazole | 97 |
| 3 | 2-[2-Hydroxy-3-(1-phenylethyl)-5-methylphenyl]-benztriazole | 83 |
| 4 | 2-(2-Hydroxy-3-cyclooctyl-5-sec-butylphenyl)-benztriazole | 94 |
| 5 | 2-(2-Hydroxy-3-cyclohexyl-5-sec-butylphenyl)-5-chlorobenztriazole | 98 |
| 6 | 2-[2-Hydroxy-3-(1-phenylethyl)-5-sec-butylphenyl]-5-chlorobenztriazole | 91 |
| 7 | 2-[2-Hydroxy-3-(1-phenylethyl)-5-sec-butylphenyl)-benztriazole | 97 |

After stoving, the sheets are exposed to light in the Weather-o-meter, and after 500, 1000 and 2000 hours the residual content of UV-absorber in the lacquer layer is measured spectrophotometrically. Table V below gives the residual content of UV-absorber after 500, 1000 and 2000 hours exposure to light, relative (a) to the content after stoving, and (b) to the amount of UV-absorber employed before stoving.

Table V

| | | Residual content in % after hrs. exposure to light. | | | | | |
|---|---|---|---|---|---|---|---|
| | | 500 | | 1000 | | 2000 | |
| No. | UV-Absorber | a | b | a | b | a | b |
| 1 | 2-(2-Hydroxy-3,5-di-tert.amylphenyl)-benztriazole (comparison compound) | 80 | 20 | 55 | 14 | 25 | 6 |
| 2 | 2-[2-Hydroxy-3-(1-phenylethyl)-5-methylphenyl]-5-chlorobenztriazole | 94 | 91 | 82 | 80 | 70 | 68 |
| 3 | 2-[2-Hydroxy-3-(1-phenylethyl)-5-methylphenyl]-benztriazole | 93 | 77 | 82 | 68 | 67 | 56 |
| 4 | 2-(2-Hydroxy-3-cyclooctyl-5-sec-butylphenyl)-benztriazole | 89 | 85 | 72 | 67 | 56 | 53 |
| 5 | 2-(2-Hydroxy-3-cyclohexyl-5-sec-butylphenyl)-5-chlorobenztriazole | 92 | 72 | 78 | 61 | 65 | 51 |
| 6 | 2-[2-Hydroxy-3-(1-phenylethyl)-5-sec-butylphenyl]-5-chlorobenztriazole | 92 | 84 | 81 | 74 | 71 | 65 |
| 7 | 2-[2-Hydroxy-3-(1-phenylethyl)-5-sec-butylphenyl]-benztriazole | 93 | 90 | 82 | 80 | 68 | 66 |

EXAMPLE 5

0.9 part (= 2% calculated relative to solids content of the lacquer) of a UV-absorber of the table which follows is added to 100 parts of an alkyd-melamine resin lacquer of the following composition: 50 parts of Beckosol 230 as a 60% strength solution in xylene (Reichhold Chemie), 30 parts of Super Beckamin 852, as a 50% strength solution in xylene (Reichhold Chemie), 10 parts of xylene and 10 parts of ethylene glycol-monomethyl ether. The resulting lacquer formulation is treated exactly as described in Example 4. The loss of UV-absorber on stoving the lacquer can be seen from Table VI below.

Table VI

| No. | UV-Absorber | Residual content after 30 mins. stoving at 140° C |
|---|---|---|
| 1 | 2-(2-Hydroxy-3,5-di-tert.amylphenyl)-benztriazole (comparison compound) | 23 |
| 2 | 2-[2-Hydroxy-3-(1-phenylethyl)-5-methylphenyl]-5-chlorobenztriazole | 92 |
| 3 | 2-[2-Hydroxy-3-(1-phenylethyl)-5-methylphenyl]-benztriazole | 79 |
| 4 | 2-(2-Hydroxy-3-cyclooctyl-5-sec-butylphenyl)-benztriazole | 91 |
| 5 | 2-(2-Hydroxy-3-cyclohexyl-5-sec-butylphenyl)-5-chlorobenztriazole | 81 |
| 6 | 2-[2-Hydroxy-3-(1-phenylethyl)-5-sec-butylphenyl]-5-chlorobenztriazole | 93 |
| 7 | 2-[2-Hydroxy-3-(1-phenylethyl)-5-sec-butylphenyl]-benztriazole | 92 |

The exposure to light, in the Weather-o-meter, of the stoved lacquer gives the residual contents of UV-absorber listed in Table VII, relative (a) to the content after stoving and (b) to the amount of UV-absorber employed before stoving.

Table VII

| No. | UV-Absorber | Residual content in % after hrs. exposure to light. | | | | | |
|-----|-------------|-----|-----|-----|-----|-----|-----|
| | | 500 | | 1000 | | 2000 | |
| | | a | b | a | b | a | b |
| 1 | 2-(2-Hydroxy-3,5-di-tert.amylphenyl-benztriazole (comparison compound) | 65 | 15 | 32 | 7 | 14 | 3 |
| 2 | 2-[2-Hydroxy-3-(1-phenylethyl)-5-methyl-phenyl]-5-chlorobenztriazole | 85 | 78 | 59 | 54 | 38 | 35 |
| 3 | 2-[2-Hydroxy-3-(1-phenylethyl)-5-methyl-phenyl]-benztriazole | 85 | 67 | 59 | 46 | 42 | 33 |
| 4 | 2-(2-Hydroxy-3-cyclooctyl-5-sec-butyl-phenyl)-benztriazole | 88 | 80 | 63 | 57 | 44 | 40 |
| 5 | 2-(2-Hydroxy-3-cyclohexyl-5-sec-butyl-phenyl)-5-chlorobenztriazole | 84 | 68 | 76 | 62 | 52 | 42 |
| 6 | 2-[2-Hydroxy-3-(1-phenylethyl)-5-sec-butylphenyl]-5-chlorobenztriazole | 86 | 80 | 81 | 75 | 68 | 63 |
| 7 | 2-[2-Hydroxy-3-1-phenylethyl)-5-sec-butylphenyl]-benztriazole | 84 | 77 | 65 | 60 | 53 | 49 |

EXAMPLE 6

1000 parts of polypropylene powder (melt index 2.5) are mixed in a drum mixer with 1 part of β-(3,5-di-tert.-butyl-4-hydroxyphenyl)-propionic acid octadecyl ester and 5 parts of a UV-absorber of Table VIII below, and are subsequently granulated in a Buss Co-kneader at a temperature of 200° C.

The resulting granules are converted in the usual manner by means of an extruder and slit die, to give a film which is subsequently cut into narrow strips, which are stretched 1:6 and wound up (gauge of the narrow strips: 700–900 den, tenacity: 5.5 – 6.5 g/den).

The narrow polypropylene strips thus produced are mounted, without tension, on sample carriers and are exposed to light in the Xenotest apparatus. After various times, 5 test specimens at a time are removed and their tenacities determined. The measure used for the protective action of the individual UV-absorbers is the exposure time, converted to a "protection factor", after which the tenacity of the narrow strips has declined by half its value before exposure to light. The values obtained are listed in Table VIII below. Here the "protective" is defined as follows:

"Protective factor" = $\frac{\text{Exposure time of the sample with UV-absorber}}{\text{Exposure time of the sample without UV-absorber}}$ (The values listed in the second column are the exposure time).

Table VIII

| No. | UV-Absorber | Hrs. of Xeno-exposure for the tenacity to decline to 50% of the initial value | Protective factor |
|-----|-------------|------|------|
| | None | 350 | 1 |
| 1 | 2-(2-Hydroxy-3,5-di-tert.-amyl-phenyl)-benztriazole (comparison compound) | 640 | 1.83 |
| 2 | 2-(2-Hydroxy-3,5-di-isopropyl-phenyl)-5-chlorobenztriazole | 660 | 1.88 |
| 3 | 2-[2-Hydroxy-3-(1-phenylethyl)-5-methylphenyl]-5-chlorobenztriazole | 710 | 2.03 |
| 4 | 2-[2-Hydroxy-3-(1-phenylethyl)-5-methylphenyl]-benztriazole | 700 | 2.0 |
| 5 | 2-(2-Hydroxy-3-tert.-amyl-5-sec-butylphenyl)-5-chlorobenztriazole | 670 | 1.91 |
| 6 | 2-(2-Hydroxy-3-cyclohexyl-5-sec-butylphenyl)-benztriazole | 700 | 2.0 |
| 7 | 2-(2-Hydroxy-3-cyclohexyl-5-sec-butylphenyl)-5-chlorobenztriazole | 730 | 2.08 |
| 8 | 2-(2-Hydroxy)-3-tert.-butyl-5-sec-butylphenyl)-benztriazole | 680 | 1.94 |

EXAMPLE 7

A solution of 15 g of acetylcellulose having an average of 2.5 acetoxy groups per glucose unit and of 0.075 g of one of the UV-absorbers listed in the table below in 85 g of acetone, is spread on a sheet of glass to give a film. The celluloseacetate films obtained after evaporation of the acetone are first dried at room temperature and then in an oven at 60° C. Samples of this 0.04 mm thick UV-filter are exposed to light in the Fade-O-Meter for 500 hours in order to measure the fastness to light of the UV-absorbers, are are tested for their residual UV-absorption. The results obtained are given in Table IX below.

It can be seen therefrom that the compounds according to the invention show better fastness to light than the previously known commercially available products (Compounds 1 - 3)

Table IX

| No. | UV-absorber | % UV-absorber after exposure to light |
|-----|-------------|------|
| 1 | 2-(2-Hydroxy-5-methylphenyl)-benztriazole (Comparison compound) | 61 |
| 2 | 2-(2-Hydroxy-3-tert.-butyl-5-methylphenyl)-5-chlorobenztriazole (Comparison compound) | 55 |
| 3 | 2-(2-Hydroxy-3,5-di-tert.-butylphenyl)-5-chlorobenztriazole (Comparison compound) | 61 |
| 4 | 2-(2-Hydroxy-5-sec-butylphenyl)-benztriazole | 74 |
| 5 | 2-(2-Hydroxy-5-isopropylphenyl)-benztriazole | 82 |

Table IX-continued

| No. | UV-absorber | % UV-absorber after exposure to light |
|---|---|---|
| 6 | 2-(2-Hydroxy-3-chloro-5-sec-butylphenylbenztriazole | 82 |
| 7 | 2-(2-Hydroxy-3-sec-butyl-5-chlorophenyl)-benztriazole | 78 |
| 8 | 2-[2-Hydroxy-3(1-phenylethyl)-5-sec-butylphenyl]-5-chlorobenztriazole | 76 |

EXAMPLE 8

100 parts of polystyrene granules are mixed dry with 0.25 part of a light protection agent of Table X below, and 0.1 part of 2,4,6-tri-tert.-butylphenol, and the mixture is injection moulded by means of an injection moulding machine to give 2 mm thick sheets.

The sheets obtained are exposed to light for 1000 hours in the Xenotest apparatus, and thereafter their yellowing is determined in terms of the yellowing factor, as follows:

$$\text{Yellowing factor } (Y.F.) = \frac{\Delta T(420) - \Delta T(680)}{T(560)} \times 100$$

wherein $\Delta T$ denotes the transmission loss at wavelength 420 and 680 nm respectively, which occurs during the exposure to light, and T (560) denotes the transmission value in per cent of the unexposed sample at 560 nm. For results, see Table XI.

Table X

| No. | UV-absorber | Y.F. |
|---|---|---|
|  | None | 8.4 |
| 1 | 2-(2-Hydroxy-5-methylphenyl)-benztriazole (comparison compound) | 0.7 |
| 2 | 2-(2-Hydroxy-5-isopropylphenyl)-benztriazole | 0.6 |

EXAMPLE 9

100 parts of methacrylic acid methyl ester, 0.5 part of a UV-absorber of Table XI below and 0.2 part of lauroyl peroxide are mixed and polymerised at a temperature of 50° – 70° C, in the form of a sheet of 2 mm thickness.

As can be seen from Table XI below, such sheets can be used as UV-filters.

Table XI

| No. | UV-absorber | % Transmission of light of wavelength | |
|---|---|---|---|
|  |  | 340 nm | 430 nm |
|  | None | 86 | 92 |
| 1 | 2-(2-Hydroxy-5-sec-butylphenyl)-benztriazole | <2 | 92 |
| 2 | 2-(2-Hydroxy-5-isopropylphenyl)-benztriazole | <2 | 92 |
| 3 | 2-(2-Hydroxy-3-chloro-5-sec-butylphenyl)-benztriazole | <2 | 92 |
| 4 | 2-(2-Hydroxy-3-sec-butyl-5-chlorophenyl)-benztriazole | <2 | 92 |
| 5 | 2-(2-Hydroxy-3,5-di-isopropylphenyl)-5-chlorobenztriazole | <2 | 92 |
| 6 | 2-(2-Hydroxy-3-tert.-butyl-5-isopropylphenyl)-benztriazole | <2 | 92 |
| 7 | 2-(2-Hydroxy-5-sec-amylphenyl)-benztriazole | <2 | 92 |
| 8 | 2-[2-Hydroxy-3-(1-phenylethyl)-5-chlorophenyl]-benztriazole | <2 | 92 |

EXAMPLE 10

A mixture of 100 parts of suspension polyvinyl chloride (K-value 60), 2.5 parts of a dialkyl-tin-mercaptide stabiliser (ADVASTAB 17 M of Deutsche Advance Produktion GmbH, Germany), 1.0 part of an epoxy stabiliser (ADVABLAST 39 of the abovementioned company), 1.0 part of a wax used as a lubricant and processing aid (Wax E of Messrs. Farbwerke Hoechst, Germany) and 0.2 part of a UV-absorber from Table XII below is converted into sheets in the usual manner on a two-roll mill.

Sample pieces of these sheets are exposed to light for 3000 hours in the Xenotest light exposure apparatus, and checked for discolourations by measuring the optical density.

The results are given in Table XII below.

Table XII

| No. | UV-absorber | Optical density after exposure to light |
|---|---|---|
|  | None (Comparison compound) | 0.28 |
| 1 | 2-(2-Hydroxy-5-methylphenyl)-benztriazole | 0.07 |
| 2 | 2-(2-Hydroxy-5-isopropylphenyl)-benztriazole | 0.06 |

EXAMPLE 11

Liquid polyester resin of low inflammability is mixed with 0.25% by weight of the UV-absorber from Table XIII below and polymerised with 1% by weight of benzoyl peroxide at 80° C to give 2.5 mm thick sheets. The sheets are post-cured at 120° C.

Sheets manufactured in this way and exposed to light show significantly less brown discolouration than sheets exposed to light in the same way but manufactured without the abovementioned UV-absorbers.

The polyester resin used was manufactured as follows: a mixture of 343 g of maleic anhydride and 428 g of tetrachlorophthalic anhydride is introduced in portions, at 80° C, into a mixture of 170 g of ethylene glycol and 292 g of diethylene glycol. After displacing the air in the reaction vessel by nitrogen, the temperature is raised to 150° C over the course of one hour and then to 210° C over the course of 9 hours, and thereafter the mixture is left for a further hour at this temperature. The composition is then cooled to 180° C, a vacuum is applied, and the pressure is slowly reduced to 100 mm Hg. These conditions are maintained until the acid number of the reaction mixture has fallen to below 50.

100 g of the polyester resin thus obtained are mixed with 50 g of styrene, and the mixture is polymerised under the conditions described above.

Similar results are obtained if instead of the tetrachlorophthalic acid and the equivalent amount of phthalic anhydride is used. Admittedly, the polyester resin obtained in that case is not of low inflammability.

If, in the above process, the styrene is replaced by methyl methacrylate, sheets are obtained which inherently have less tendency to a brown discolouration and which can furthermore be stabilised more easily.

The measurement data given in Table XIII below show that the new compounds display a better protective action than the previously known commercially available product (Compound 1).

Table XIII

| No. | UV-absorber | Transmission loss* at 440 nm after 1000 hrs. exposure to light in the Fade-o-Meter |
| --- | --- | --- |
|  | None | 25 |
| 1 | 2-(2-Hydroxy-5-methylphenyl)-benztriazole (Comparison compound) | 5 |
| 2 | 2-(2-Hydroxy-5-sec-butylphenyl)-benztriazole | 2.5 |
| 3 | 2-(2-Hydroxy-3-tert.-butyl-5-sec-butylphenyl)-benztriazole | 1.5 |
| 4 | 2-(2-Hydroxy-3-isopropylphenyl)-benztriazole | 2.5 |
| 5 | 2-[2-Hydroxy-3-(1-phenylethyl)-5-methylphenyl]-benztriazole | 3.0 |
| 6 | 2-[2-Hydroxy-3-(1-phenylethyl)-5-methylphenyl]-5-chlorobenztriazole | 2.5 |

*Transmission loss = difference in the percentage transmission of the test specimen before and after exposure to light.

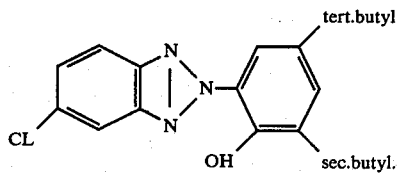

What we claim:
1. A compound of the formula

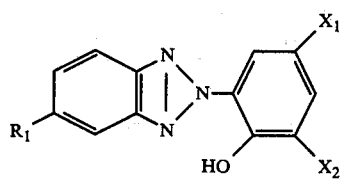

in which
(a) one of $X_1$ and $X_2$ denotes a secondary alkyl selected from the group consisting of isopropyl or secondary butyl, the other of $X_1$ and $X_2$ denotes secondary-butyl, tert. butyl, tert. amyl, tert. octyl, secondary-nonyl, tertiary. nonyl, 1-phenylethyl, cyclohexyl, or cyclooctyl
(b) one of $X_1$ and $X_2$ denotes 1-phenylethyl, the other of $X_1$ and $X_2$ denotes methyl; and $R_1$ denotes hydrogen or chloro.

2. A compound according to claim 1 which is

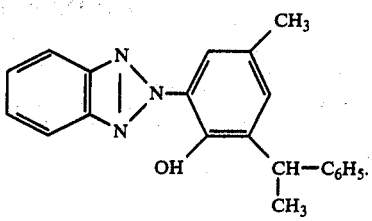

3. A compound according to claim 1 which is

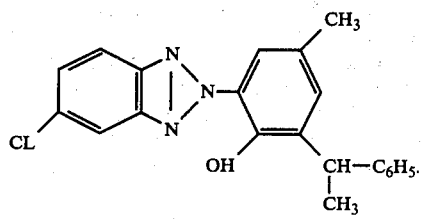

4. A compound according to claim 1 which is

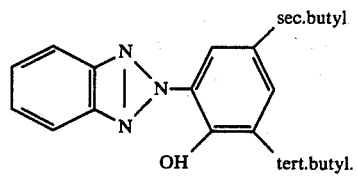

5. A compound according to claim 1 which is

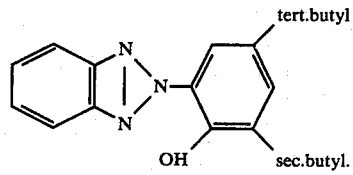

6. A compound according to claim 1 which is